(12) United States Patent
Segall et al.

(10) Patent No.: US 10,506,821 B2
(45) Date of Patent: Dec. 17, 2019

(54) PRODUCTION OF SOLUBLE PROTEIN SOLUTIONS FROM PULSES

(75) Inventors: Kevin I. Segall, Winnipeg (CA); Martin Schweizer, Winnipeg (CA)

(73) Assignee: BURCON MUTRASCIENCE (MB) CORP., Winnipeg, MB (CA)

(*) Notice: Subject to any disclaimer, the term of this patent is extended or adjusted under 35 U.S.C. 154(b) by 0 days.

(21) Appl. No.: 13/556,357

(22) Filed: Jul. 24, 2012

(65) Prior Publication Data

US 2013/0189408 A1   Jul. 25, 2013

Related U.S. Application Data

(63) Continuation-in-part of application No. 13/289,264, filed on Nov. 4, 2011, now abandoned, which is a continuation-in-part of application No. 13/103,528, filed on May 9, 2011, now abandoned.

(60) Provisional application No. 61/344,013, filed on May 7, 2010.

(51) Int. Cl.
| | | |
|---|---|---|
| *A23J 1/14* | (2006.01) | |
| *A23L 2/66* | (2006.01) | |
| *A23J 3/14* | (2006.01) | |
| *C07K 14/415* | (2006.01) | |
| *A21D 2/26* | (2006.01) | |

(52) U.S. Cl.
CPC ............... *A23J 1/14* (2013.01); *A21D 2/266* (2013.01); *A23J 3/14* (2013.01); *A23L 2/66* (2013.01); *C07K 14/415* (2013.01); *A23V 2002/00* (2013.01); *A23V 2300/14* (2013.01)

(58) Field of Classification Search
CPC ...... A23J 1/14; A23J 3/14; A23L 2/66; C07K 14/415; A21D 2/266; A23V 2002/00; A23V 2300/14; A23V 2200/33
See application file for complete search history.

(56) References Cited

U.S. PATENT DOCUMENTS

| 4,169,090 A | 9/1979 | Murray et al. |
| 4,208,323 A * | 6/1980 | Murray et al. ............... 530/372 |
| 5,844,086 A | 12/1998 | Murray |
| 6,005,076 A | 12/1999 | Murray |
| 2005/0123649 A1 * | 6/2005 | Benitez et al. ............... 426/72 |
| 2005/0255226 A1 | 11/2005 | Schweizer et al. |
| 2007/0014909 A1 | 1/2007 | Mai et al. |
| 2007/0065567 A1 | 3/2007 | Segall et al. |
| 2008/0280024 A1 | 11/2008 | Harle et al. |
| 2010/0098818 A1 * | 4/2010 | Schweizer et al. ........... 426/254 |
| 2011/0038993 A1 | 2/2011 | Schweizer et al. |
| 2011/0274797 A1 | 11/2011 | Segall et al. |
| 2013/0129901 A1 | 5/2013 | Segall et al. |

FOREIGN PATENT DOCUMENTS

| WO | WO2010/045727 | 4/2010 |
| WO | WO2010/083612 | 7/2010 |

OTHER PUBLICATIONS

Bacon, JR et al. Preparation of transparent pea protein gels: a comparison of isolation procedures. International Journal of Food Science and Technology (1 990) 25,527-537.*
Bacon et al. International Journal of Food Science and Technology (1990) 25,527-537.*
https://www.foodnavigator.com. Halliday "New pea protein process aims to grow market" Apr. 28, 2010 (Year: 2010).*
Friedman, M., Brandon, DL. Nutritional and health benefits of soy proteins. J Agric Food Chem. Mar. 2001:49(3):1069-86.
Joyce Boye et al. Pulse Proteins: Processing, characterization, functional properties and applications in food and feed. Food Research International 43(2010) 414-431.
Tian, Shaojun. The Isolation, Modification and Evaluation of Field Pea Proteins and Their Application in Foods, Dec. 1998, Victoria University of Technology, Australia.
Gelski, Jeff. Eliminating the Pea Flavor in Pea Protein, Food Business News https://www.foodbusinessnews.net/articles/11344-eliminating-the-pea-flavor-in-pea-protein.
Michail, Niamh. Flavour Pairing With Plant Proteins. https://www.foodnavigator.com/Article/2017/09/01/Flavour-pairing-with-plant-proteins-What-s-best-for-your-product.
Phillips, David. Flavor Modulation with High Expectation. https://www.foodprocessing.com/articles/2014/flavor-modulation-with-high-expectation/.
Crane, Michael. Pea Protein is Coming Up Strong. http://www.nutritionaloutlook.com/protein/pea-protein-coming-strong.

* cited by examiner

*Primary Examiner* — Subbalakshmi Prakash

(57) ABSTRACT

A pulse protein product, which may be an isolate, produces heat-stable solutions at low pH values and is useful for the fortification of acidic beverages such as soft drinks and sports drinks without precipitation of protein. The pulse protein product is obtained by extracting a pulse protein source material with an aqueous calcium salt solution to form an aqueous pulse protein solution, separating the aqueous pulse protein solution from residual pulse protein source, adjusting the pH of the aqueous pulse protein solution to a pH of about 1.5 to about 4.4 to produce an acidified pulse protein solution, which may be dried, following optional concentration and diafiltration, to provide the pulse protein product.

29 Claims, No Drawings

PRODUCTION OF SOLUBLE PROTEIN SOLUTIONS FROM PULSES

REFERENCE TO RELATED APPLICATION

This application is a continuation-in-part of U.S. patent application Ser. No. 13/289,264 filed Nov. 4, 2011, which itself is a continuation-in-part of U.S. patent application Ser. No. 13/103,528 filed May 9, 2011, which itself claims priority under 35 USC 119(e) from U.S. Provisional Patent Application No. 61/344,013 filed May 7, 2010.

FIELD OF INVENTION

The present invention is directed to the production of protein solutions from pulses and to novel pulse protein products.

BACKGROUND TO THE INVENTION

In U.S. patent application Ser. No. 12/603,087 filed Oct. 21, 2009 (US Patent Publication No. 2010-0098818 published Apr. 22, 2010), Ser. No. 12/923,897 filed Oct. 13, 2010 (US Patent Publication No. 2011-0038993 published Feb. 11, 2011) and Ser. No. 12/998,422 filed Jun. 1, 2011 (US Patent Publication No. 2011-0236556 published Sep. 29, 2011), assigned to the assignee hereof and the disclosures of which are incorporated herein by reference, there is described the production of soy protein products having a protein content of at least about 60 wt % (N×6.25) on a dry weight basis (d.b.), preferably at least about 90 wt %, which produce transparent, heat stable solutions at low pH values and which may be used for protein fortification of soft drinks, as well as other aqueous systems, without precipitation of protein.

The soy protein product is produced by extracting a soy protein source with an aqueous calcium chloride solution to cause solubilization of soy protein from the protein source and to form an aqueous soy protein solution, separating the aqueous soy protein solution from residual soy protein source, optionally diluting the soy protein solution, adjusting the pH of the aqueous soy protein solution to a pH of about 1.5 to about 4.4, preferably about 2 to about 4, to produce an acidified clear soy protein solution, optionally concentrating the aqueous clear protein solution while maintaining the ionic strength substantially constant by using a selective membrane technique, optionally diafiltering the concentrated soy protein solution, and optionally drying the concentrated and optionally diafiltered soy protein solution.

SUMMARY OF THE INVENTION

It has been found that this procedure and modifications thereof, may be used to form acid soluble protein products from pulses, including lentils, chickpeas, dry peas and dry beans.

The novel pulse protein products provided herein have a unique combination of parameters not found in other pulse protein products. The products are completely soluble in aqueous solution at acid pH values less than about 4.4 and are heat stable in this pH range permitting thermal processing of aqueous solutions of the products, such as hot fill applications. Given the complete solubility of the products, no stabilizers or other additives are necessary to maintain the protein in solution or suspension. The pulse protein products have been described as having a clean flavour and no off odours. The products are low in phytic acid, generally less than about 1.5 wt %, preferably less than about 0.5 wt %. No enzymes are required in the production of the pulse protein products. The pulse protein products are preferably isolates having a protein content of at least about 90 wt %, preferably at least about 100 wt % (N×6.25) d.b.

Accordingly, in one aspect of the present invention, there is provided a method of producing a pulse protein product having a protein content of at least about 60 wt %, preferably at least about 90 wt %, (N×6.25) on a dry weight basis, which comprises:

(a) extracting a pulse protein source with an aqueous calcium salt solution, preferably an aqueous calcium chloride solution, to cause solubilization of pulse protein from the protein source and to form an aqueous pulse protein solution, (b) separating the aqueous pulse protein solution from residual pulse protein source, (c) optionally diluting the aqueous pulse protein solution, (d) adjusting the pH of the aqueous pulse protein solution to a pH of about 1.5 to about 4.4, preferably about 2 to about 4, to produce an acidified pulse protein solution, (e) optionally clarifying the acidified pulse protein solution if it is not already clear, (f) alternatively from steps (b) to (e), optionally, diluting and then adjusting the pH of the combined aqueous pulse protein solution and residual pulse protein source to a pH of about 1.5 to about 4.4, preferably about 2 to about 4, then separating the acidified, preferably clear, pulse protein solution from residual pulse protein source, (g) optionally concentrating the aqueous pulse protein solution while maintaining the ionic strength substantially constant by a selective membrane technique, (h) optionally diafiltering the concentrated pulse protein solution, and (i) optionally drying the concentrated and optionally diafiltered pulse protein solution.

The pulse protein product preferably is an isolate having a protein content of at least about 90 wt %, preferably at least about 100 wt %, (N×6.25) d.b.

The present invention further provides a novel pulse protein product having a protein content of at least about 60 wt %, preferably at least about 90 w/t %, more preferably at least about 100 wt % (N×6.25) d.b., and which is water soluble and forms heat stable solutions at acid pH values of less than about 4.4 and is useful for the protein fortification of aqueous systems, including soft drinks and sport drinks, without leading to protein precipitation. The pulse protein product is also low in phytic acid content, generally less than about 1.5% by weight, preferably less than about 0.5% by weight. The pulse protein in the product is not hydrolyzed.

Thus, in another aspect to the present invention, there is provided a pulse protein product having a protein content of at least about 60 wt % (N×6.25) d.b., preferably a pulse protein isolate having a protein content of at least about 90 wt % (N×6.25) d.b., more preferably at least about 100 wt % (N×6.25) d.b., which is substantially completely soluble in an aqueous medium at a pH of less than about 4.4, preferably about 1.5 to about 4.4.

The pulse protein product provided herein may be provided as an aqueous solution thereof, preferably having a high degree of clarity at acid pH values, generally less than about 4.4, preferably about 1.5 to about 4.4, and which is heat stable at these pH values.

The novel pulse protein product of the invention can be blended with powdered drinks for the formation of aqueous soft drinks or sports drinks by dissolving the same in water. Such blend may be a powdered beverage.

While the present invention refers mainly to the production of pulse protein isolate, it is contemplated that pulse protein products of lesser purity may be provided having similar properties to the pulse protein isolate. Such lesser purity products may have a protein concentration of at least about 60% by weight (N×6.25) d.b.

In another aspect of the present invention, there is provided an aqueous solution of the pulse protein product provided herein which is heat stable at a pH of less than about 4.4. The aqueous solution may be a beverage, which may be a clear beverage in which the pulse protein product is completely soluble and transparent or the aqueous solution may be an opaque beverage in which the pulse protein product does or does not contribute to the opacity. The aqueous solutions have excellent flavor attributes and, in informal taste panel tests, exhibited a cleaner taste than aqueous solutions of commercial pulse protein products.

The pulse protein product of the invention has a molecular weight profile, determined using the methods described in Example 26 below, which is:
  about 60 to about 92%, preferably about 75 to about 85%, greater than about 100,000 Da
  about 7 to about 26%, preferably about 10 to about 18%, from about 15,000 to about 100,000 Da.
  about 1 to about 8%, preferably about 2 to about 5%, from about 5,000 to about 15,000 Da
  0 to about 6%, preferably 1 to about 4%, from about 1,000 to about 5,000 Da.

The pulse protein product is preferably a yellow pea protein product.

In a further aspect of the present invention, there is provided a pulse protein product, preferably a yellow pea protein product, having a protein content of at least about 60 wt % (N×6.25) d.b., preferably at least about 90 wt %, more preferably at least about 100 wt %, which has a solubility at 1% protein w/v in water at a pH of about 2 to about 4 greater than about 90%, as determined by the methods described in Example 27 below.

Additionally, the present invention provides a pulse protein product, preferably a yellow pea protein product, having a protein content of at least about 60 wt % (N×6.25) d.b., preferably at least about 90 wt %, more preferably at least about 100 wt %0, which has an absorbance of visible light at 600 nm (A600) for a 1% protein w/v aqueous solution at a pH of about 2 to about 4 of less than 0.150, preferably less than about 0.100, more preferably less than 0.050, as determined by the method described in Example 29 below.

In accordance with a further embodiment of the invention, there is provided a pulse protein product, preferably a yellow pea protein product, having a protein content of at least about 60 wt % (N×6.25) d.b., preferably at least about 90 wt %, more preferably at least about 100 wt %, which has a haze reading for a 1% protein w/v aqueous solution at a pH of about 2 to about 4, of less than about 15%, preferably less than about 10% and more preferably less than about 5%, as determined by the method described in Example 29 below.

In accordance with a yet further embodiment of the invention, there is provided a pulse protein product, preferably a yellow pea protein product, having a protein content of at least about 60 wt % (N×6.25) d.b., preferably at least about 90 wt %, more preferably at least about 100 wt %, which has a haze reading for a solution thereof in water at 2% protein w/v, after heat treatment at 95° C. for 30 seconds of less than about 15%, preferably less than about 10% and more preferably less than 5%, as determined by the method described in Example 30 below.

As may be seen from the data presented below, the aqueous solutions of the pulse protein products provide herein are practically colourless, unlike aqueous solutions provided from typical commercial pulse protein products. It will be appreciated that a completely clear, colourless solution would provide colorimeter readings of L*=100, a*=0 and b*=0. Based on the data generated herein, in accordance with another aspect of the present invention, there is provided a novel pulse protein product, preferably a yellow pea protein product, having a protein content of at least 60 wt % (N×6.25) d.b., preferably at least about 90 wt %, more preferably at least about 100 wt %, which has colorimeter readings for a solution thereof in water, prepared by dissolving sufficient pulse protein product to supply 3.2 g of protein per 100 ml of water used, which are a combination of:
  L* about 82 to about 100, preferably about 92 to about 100
  a* about −2 to about 5, preferably about −1 to about 1
  b* about 0 to about 30, preferably about 0 to about 14.

The pulse protein products produced according to the process herein are suitable, not only for protein fortification of acid media, but may be used in a wide variety of conventional applications of protein products, including but not limited to protein fortification of processed foods and beverages, emulsification of oils, as a body former in baked goods and foaming agent in products which entrap gases. In addition, the pulse protein isolates may be formed into protein fibers, useful in meat analogs and may be used as an egg white substitute or extender in food products where egg white is used as a binder. The pulse protein products may also be used in nutritional supplements. The pulse protein products may also be used in dairy analogue products or products that are dairy/plant ingredient blends. Other uses of the pulse protein products are in pet foods, animal feed and in industrial and cosmetic applications and in personal care products.

GENERAL DESCRIPTION OF THE INVENTION

The initial step of the process of providing the pulse protein products involves solubilizing pulse protein from a pulse protein source. The pulses to which the invention may be applied include, but are not limited to lentils, chickpeas, dry peas and dry beans. The pulse protein source may be pulses or any pulse product or by-product derived from the processing of pulses. For example, the pulse protein source may be a flour prepared by grinding an optionally dehulled pulse. As another example, the pulse protein source may be a protein-rich pulse fraction formed by dehulling and grinding a pulse and then air classifying the dehulled and ground material into starch-rich and protein-rich fractions. The pulse protein product recovered from the pulse protein source may be the protein naturally occurring in pulses or the proteinaceous material may be a protein modified by genetic manipulation but possessing characteristic hydrophobic and polar properties of the natural protein.

Protein solubilization from the pulse protein source material is effected most conveniently using calcium chloride solution, although solutions of other calcium salts, may be used. In addition, other alkaline earth metal compounds may be used, such as magnesium salts. Further, extraction of the pulse protein from the pulse protein source may be effected using calcium salt solution in combination with another salt solution, such as sodium chloride. Additionally, extraction of the pulse protein from the pulse protein source may be effected using water or other salt solution, such as sodium chloride, with calcium salt subsequently being added to the aqueous pulse protein solution produced in the extraction step. Precipitate formed upon addition of the calcium salt is removed prior to subsequent processing.

As the concentration of the calcium salt solution increases, the degree of solubilization of protein from the pulse protein source initially increases until a maximum value is achieved. Any subsequent increase in salt concentration does not increase the total protein solubilized. The concentration of calcium salt solution which causes maximum protein solubilization varies depending on the salt concerned. It is usually preferred to utilize a concentration value less than about 1.0 M, and more preferably a value of about 0.10 to about 0.15 M.

In a batch process, the salt solubilization of the protein is effected at a temperature of from about 1° to about 100° C., preferably about 15° C. to about 65° C., more preferably about 20° to about 35° C., preferably accompanied by agitation to decrease the solubilization time, which is usually about 1 to about 60 minutes. It is preferred to effect the solubilization to extract substantially as much protein from the pulse protein source as is practicable, so as to provide an overall high product yield.

In a continuous process, the extraction of the protein from the pulse protein source is carried out in any manner consistent with effecting a continuous extraction of protein from the pulse protein source. In one embodiment, the pulse protein source is continuously mixed with the calcium salt solution and the mixture is conveyed through a pipe or conduit having a length and at a flow rate for a residence time sufficient to effect the desired extraction in accordance with the parameters described herein. In such a continuous procedure, the salt solubilization step is effected in a time of about 1 minute to about 60 minutes, preferably to effect solubilization to extract substantially as much protein from the pulse protein source as is practicable. The solubilization in the continuous procedure is effected at temperatures between about 1° and about 100° C., preferably between about 15° C. and about 65° C., more preferably between about 20° and about 35° C.

The extraction is generally conducted at a pH of about 4.5 to about 11, preferably about 5 to about 7. The pH of the extraction system (pulse protein source and calcium salt solution) may be adjusted to any desired value within the range of about 4.5 to about 11 for use in the extraction step by the use of any convenient food grade acid, usually hydrochloric acid or phosphoric acid, or food grade alkali, usually sodium hydroxide, as required.

The concentration of pulse protein source in the calcium salt solution during the solubilization step may vary widely. Typical concentration values are about 5 to about 15% w/v.

The protein extraction step with the aqueous salt solution has the additional effect of solubilizing fats which may be present in the pulse protein source, which then results in the fats being present in the aqueous phase.

The protein solution resulting from the extraction step generally has a protein concentration of about 5 to about 50 g/L, preferably about 10 to about 50 g/L.

The aqueous calcium salt solution may contain an antioxidant. The antioxidant may be any convenient antioxidant, such as sodium sulfite or ascorbic acid. The quantity of antioxidant employed may vary from about 0.01 to about 1 wt % of the solution, preferably about 0.05 wt %. The antioxidant serves to inhibit oxidation of any phenolics in the protein solution.

The aqueous phase resulting from the extraction step then may be separated from the residual pulse protein source, in any convenient manner, such as by employing a decanter centrifuge, followed by disc centrifugation and/or filtration, to remove residual pulse protein source material. The separation step may be conducted at any temperature within the range of about 1° to about 100° C., preferably about 15° to about 65° C., more preferably about 50° to about 60° C. Alternatively, the optional dilution and acidification steps described below may be applied to the mixture of aqueous pulse protein solution and residual pulse protein source, with subsequent removal of the residual pulse protein source material by the separation step described above. The separated residual pulse protein source may be dried for disposal or further processed, such as to recover starch and/or residual protein. Residual protein may be recovered by re-extracting the separated residual pulse protein source with fresh calcium salt solution and the protein solution yielded upon clarification combined with the initial protein solution for further processing as described below. Alternatively, the separated residual pulse protein source may be processed by a conventional isoelectric precipitation process or any other convenient procedure to recover residual protein.

The aqueous pulse protein solution may be treated with an anti-foamer, such as any suitable food-grade, non-silicone based anti-foamer, to reduce the volume of foam formed upon further processing. The quantity of anti-foamer employed is generally greater than about 0.0003% w/v. Alternatively, the anti-foamer in the quantity described may be added in the extraction steps.

The separated aqueous pulse protein solution may be subject to a defatting operation, if required, as described in U.S. Pat. Nos. 5,844,086 and 6,005,076, assigned to the assignee hereof and the disclosures of which are incorporated herein by reference. Alternatively, defatting of the separated aqueous pulse protein solution may be achieved by any other convenient procedure.

The aqueous pulse protein solution may be treated with an adsorbent, such as powdered activated carbon or granulated activated carbon, to remove colour and/or odour compounds. Such adsorbent treatment may be carried out under any convenient conditions, generally at the ambient temperature of the separated aqueous protein solution. For powdered activated carbon, an amount of about 0.025% to about 5% w/v, preferably about 0.05% to about 2% w/v, is employed. The adsorbing agent may be removed from the pulse protein solution by any convenient means, such as by filtration.

The resulting aqueous pulse protein solution may be diluted generally with about 0.1 to about 10 volumes, preferably about 0.5 to about 2 volumes of aqueous diluent, in order to decrease the conductivity of the aqueous pulse protein solution to a value of generally below about 105 mS, preferably about 4 to about 21 mS. Such dilution is usually effected using water, although dilute salt solution, such as sodium chloride or calcium chloride, having a conductivity up to about 3 mS, may be used.

The diluent with which the pulse protein solution is mixed generally has the same temperature as the pulse protein solution, but the diluent may have a temperature of about 1° to about 100° C., preferably about 15° to about 65° C., more preferably about 50° to about 60° C.

The optionally diluted pulse protein solution then is adjusted in pH to a value of about 1.5 to about 4.4, preferably about 2 to about 4, by the addition of any suitable food grade acid, such as hydrochloric acid or phosphoric acid, to result in an acidified aqueous pulse protein solution, preferably a clear acidified aqueous pulse protein solution. The acidified aqueous pulse protein solution has a conductivity of generally below about 110 mS for a diluted pulse protein solution, or generally below about 115 mS for an undiluted pulse protein solution, in both cases preferably about 4 to about 26 mS.

As mentioned above, as an alternative to the earlier separation of the residual pulse protein source, the aqueous pulse protein solution and the residual pulse protein source material, may be optionally diluted and acidified together and then the acidified aqueous pulse protein solution is clarified and separated from the residual pulse protein source material by any convenient technique as discussed above. The acidified aqueous pulse protein solution may optionally be defatted, optionally treated with an adsorbent and optionally treated with defoamer as described above.

The acidified aqueous pulse protein solution may be subjected to a heat treatment to inactivate heat labile anti-nutritional factors, such as trypsin inhibitors, present in such solution as a result of extraction from the pulse protein source material during the extraction step. Such a heating step also provides the additional benefit of reducing the microbial load. Generally, the protein solution is heated to a temperature of about 70° to about 160° C., preferably about 80° to about 120° C., more preferably about 85° to about 95, for about 10 seconds to about 60 minutes, preferably about 10 seconds to about 5 minutes, more preferably about 30 seconds to about 5 minutes. The heat treated acidified pulse protein solution then may be cooled for further processing as described below, to a temperature of about 2° to about 65° C., preferably about 50° C. to about 60° C.

If the optionally diluted, acidified and optionally heat treated pulse protein solution is not transparent it may be clarified by any convenient procedure such as filtration or centrifugation.

The resulting acidified aqueous pulse protein solution may be directly dried to produce a pulse protein product. In order to provide a pulse protein product having a decreased impurities content and a reduced salt content, such as a pulse protein isolate, the acidified aqueous pulse protein solution may be processed as described below prior to drying.

The acidified aqueous pulse protein solution may be concentrated to increase the protein concentration thereof while maintaining the ionic strength thereof substantially constant. Such concentration generally is effected to provide a concentrated pulse protein solution having a protein concentration of about 50 to about 300 g/L, preferably about 100 to about 200 g/L.

The concentration step may be effected in any convenient manner consistent with batch or continuous operation, such as by employing any convenient selective membrane technique, such as ultrafiltration or diafiltration, using membranes, such as hollow-fibre membranes or spiral-wound membranes, with a suitable molecular weight cut-off, such as about 1,000 to about 1,000,000 Daltons, preferably about 3,000 to about 100,000 Daltons, having regard to differing membrane materials and configurations, and, for continuous operation, dimensioned to permit the desired degree of concentration as the aqueous protein solution passes through the membranes.

As is well known, ultrafiltration and similar selective membrane techniques permit low molecular weight species to pass therethrough while preventing higher molecular weight species from so doing. The low molecular weight species include not only the ionic species of the salt but also low molecular weight materials extracted from the source material, such as carbohydrates, pigments, low molecular weight proteins and anti-nutritional factors, such as trypsin inhibitors, which are themselves low molecular weight proteins. The molecular weight cut-off of the membrane is usually chosen to ensure retention of a significant proportion of the protein in the solution, while permitting contaminants to pass through having regard to the different membrane materials and configurations.

The concentrated pulse protein solution then may be subjected to a diafiltration step using water or a dilute saline solution. The diafiltration solution may be at its natural pH or at a pH equal to that of the protein solution being diafiltered or at any pH value in between. Such diafiltration may be effected using from about 1 to about 40 volumes of diafiltration solution, preferably about 2 to about 25 volumes of diafiltration solution. In the diafiltration operation, further quantities of contaminants are removed from the aqueous pulse protein solution by passage through the membrane with the permeate. This purifies the aqueous protein solution and may also reduce its viscosity. The diafiltration operation may be effected until no significant further quantities of contaminants or visible color are present in the permeate or until the retentate has been sufficiently purified so as, when dried, to provide a pulse protein isolate with a protein content of at least about 90 wt % (N×6.25) d.b. Such diafiltration may be effected using the same membrane as for the concentration step. However, if desired, the diafiltration step may be effected using a separate membrane with a different molecular weight cut-off, such as a membrane having a molecular weight cut-off in the range of about 1,000 to about 1,000,000 Daltons, preferably about 3,000 to about 100,000 Daltons, having regard to different membrane materials and configuration.

Alternatively, the diafiltration step may be applied to the acidified aqueous protein solution prior to concentration or to partially concentrated acidified aqueous protein solution. Diafiltration may also be applied at multiple points during the concentration process. When diafiltration is applied prior to concentration or to the partially concentrated solution, the resulting diafiltered solution may then be additionally concentrated. The viscosity reduction achieved by diafiltering multiple times as the protein solution is concentrated may allow a higher final, fully concentrated protein concentration to be achieved. This reduces the volume of material to be dried.

The concentration step and the diafiltration step may be effected herein in such a manner that the pulse protein product subsequently recovered contains less than about 90 wt % protein (N×6.25) d.b., such as at least about 60 wt % protein (N×6.25) d.b. By partially concentrating and/or partially diafiltering the aqueous pulse protein solution, it is possible to only partially remove contaminants. This protein solution may then be dried to provide a pulse protein product with lower levels of purity. The pulse protein product is highly soluble and able to produce protein solutions, preferably clear protein solutions, under acidic conditions.

An antioxidant may be present in the diafiltration medium during at least part of the diafiltration step. The antioxidant may be any convenient antioxidant, such as sodium sulfite or ascorbic acid. The quantity of antioxidant employed in the diafiltration medium depends on the materials employed and may vary from about 0.01 to about 1 wt %, preferably about 0.05 wt %. The antioxidant serves to inhibit the oxidation of any phenolics present in the pulse protein solution.

The optional concentration step and the optional diafiltration step may be effected at any convenient temperature, generally about 2° to about 65° C., preferably about 50° to about 60° C., and for the period of time to effect the desired degree of concentration and diafiltration. The temperature and other conditions used to some degree depend upon the membrane equipment used to effect the membrane processing, the desired protein concentration of the solution and the efficiency of the removal of contaminants to the permeate.

As alluded to earlier, pulses contain anti-nutritional trypsin inhibitors. The level of trypsin inhibitor activity in the final pulse protein product can be controlled by the manipulation of various process variables.

As noted above, heat treatment of the acidified aqueous pulse protein solution may be used to inactivate heat-labile trypsin inhibitors. The partially concentrated or fully concentrated acidified pulse protein solution may also be heat treated to inactivate heat labile trypsin inhibitors. When the heat treatment is applied to the partially concentrated acidified pulse protein solution, the resulting heat treated solution may then be additionally concentrated.

In addition, the concentration and/or diafiltration steps may be operated in a manner favorable for removal of trypsin inhibitors in the permeate along with the other contaminants. Removal of the trypsin inhibitors is promoted by using a membrane of larger pore size, such as 30,000 to 1,000,000 Da, operating the membrane at elevated temperatures, such as about 30° to about 65° C., preferably about 50° to about 60° C. and employing greater volumes of diafiltration medium, such as 10 to 40 volumes.

Acidifying and membrane processing the pulse protein solution at a lower pH, such as 1.5 to 3, may reduce the trypsin inhibitor activity relative to processing the solution at higher pH, such as 3 to 4.4. When the protein solution is concentrated and/or diafiltered at the low end of the pH range, it may be desired to raise the pH of the solution prior to drying. The pH of the concentrated and/or diafiltered protein solution may be raised to the desired value, for example pH 3, by the addition of any convenient food grade alkali, such as sodium hydroxide.

Further, a reduction in trypsin inhibitor activity may be achieved by exposing pulse materials to reducing agents that disrupt or rearrange the disulfide bonds of the inhibitors. Suitable reducing agents include sodium sulfite, cysteine and N-acetylcysteine.

The addition of such reducing agents may be effected at various stages of the overall process. The reducing agent may be added with the pulse protein source material in the extraction step, may be added to the clarified aqueous pulse protein solution following removal of residual pulse protein source material, may be added to the diafiltered retentate before drying or may be dry blended with the dried pulse protein product. The addition of the reducing agent may be combined with the heat treatment step and membrane processing steps, as described above.

If it is desired to retain active trypsin inhibitors in the protein solution, this can be achieved by eliminating or reducing the intensity of the heat treatment step, not utilizing reducing agents, operating the optional concentration and optional diafiltration steps at the higher end of the pH range, such as 3 to 4.4, utilizing a concentration and diafiltration membrane with a smaller pore size, operating the membrane at lower temperatures and employing fewer volumes of diafiltration medium.

The optionally concentrated and optionally diafiltered protein solution may be subject to a further defatting operation, if required, as described in U.S. Pat. Nos. 5,844,086 and 6,005,076. Alternatively, defatting of the optionally concentrated and optionally diafiltered protein solution may be achieved by any other convenient procedure.

The optionally concentrated and optionally diafiltered aqueous protein solution may be treated with an adsorbent, such as powdered activated carbon or granulated activated carbon, to remove color and/or odour compounds. Such adsorbent treatment may be carried out under any convenient conditions, generally at the ambient temperature of the protein solution. For powdered activated carbon, an amount of about 0.025% to about 5% w/v, preferably about 0.05% to about 2% w/v, is employed. The adsorbent may be removed from the pulse protein solution by any convenient means, such as by filtration.

The optionally concentrated and optionally diafiltered aqueous pulse protein solution may be dried by any convenient technique, such as spray drying or freeze drying. A pasteurization step may be effected on the pulse protein solution prior to drying. Such pasteurization may be effected under any desired pasteurization conditions. Generally, the optionally concentrated and optionally diafiltered pulse protein solution is heated to a temperature of about 55° to about 70° C., preferably about 60° to about 65° C., for about 30 seconds to about 60 minutes, preferably about 10 minutes to about 15 minutes. The pasteurized pulse protein solution then may be cooled for drying, preferably to a temperature of about 25° to about 40° C.

The dry pulse protein product has a protein content greater than about 60 wt %. Preferably, the dry pulse protein product is an isolate with a protein content in excess of about 90 wt % protein, preferably at least about 100 wt %, (N×6.25) d.b.

The pulse protein product produced herein is soluble in an acidic aqueous environment, making the product ideal for incorporation into beverages, both carbonated and uncarbonated, to provide protein fortification thereto. Such beverages have a wide range of acidic pH values, ranging from about 2.5 to about 5. The pulse protein product provided herein may be added to such beverages in any convenient quantity to provide protein fortification to such beverages, for example, at least about 5 g of the pulse protein per serving. The added pulse protein product dissolves in the beverage and the opacity of the beverage is not increased by thermal processing. The pulse protein product may be blended with dried beverage prior to reconstitution of the beverage by dissolution in water. In some cases, modification to the normal formulation of the beverages to tolerate the composition of the invention may be necessary where components present in the beverage may adversely affect the ability of the composition of the invention to remain dissolved in the beverage.

EXAMPLES

Example 1

This Example evaluates the protein extractability of lentils, chickpeas and dry peas and the effect of acidification on the clarity of protein solutions resulting from the extraction step.

Dry lentils, chickpeas, yellow split peas and green split peas were purchased in whole form and ground using a Bamix chopper until in the form of a relatively fine powder. The extent of grinding was not controlled by time or particle size. Ground material (10 g) was extracted with 0.15M $CaCl_2$ (100 ml) for 30 minutes on a magnetic stirrer at room temperature. The extract was separated from the spent material by centrifugation at 10,200 g for 10 minutes and then further clarified by filtration with a 0.45 µm pore size syringe filter. The ground starting material and the clarified extract were tested for protein content using a Loco FP 528 Nitrogen Determinator. The clarity of the extract at full strength and diluted with 1 volume of reverse osmosis purified (RO) water was determined by measuring the absorbance at 600 nm (A600). The full strength and diluted solutions were then adjusted to pH 3 with HCl and the A600 measured again. In this and other Examples where solution clarity was assessed by A600 measurement, water was used to blank the spectrophotometer.

The protein contents and apparent extractabilities determined for each protein source are shown in Table 1.

TABLE 1

Protein content and apparent extractability of protein sources

| protein source | protein content (%) | apparent extractability (%) |
|---|---|---|
| lentil | 24.20 | 47.5 |
| chickpeas | 18.97 | 52.2 |
| yellow split peas | 23.07 | 59.4 |
| green split peas | 22.38 | 64.3 |

As may be seen from the results in Table 1, the apparent extractability of all the protein sources was quite good.

Clarity of the full strength and diluted extract samples before and after acidification are shown in Table 2.

TABLE 2

Effect of acidification on clarity of diluted and undiluted extract samples - calcium chloride extraction

| | undiluted | | | | diluted | | | |
|---|---|---|---|---|---|---|---|---|
| sample | initial pH | initial A600 | final pH | final A600 | initial pH | initial A600 | final pH | final A600 |
| lentils | 5.22 | 0.093 | 3.04 | 0.253 | 5.30 | 1.196 | 2.96 | 0.037 |
| chickpeas | 5.15 | 0.189 | 3.07 | 0.228 | 5.25 | 2.714 | 2.79 | 0.099 |
| yellow split peas | 5.21 | 0.250 | 3.14 | 0.828 | 5.28 | 2.334 | 3.11 | 0.250 |
| green split peas | 5.23 | 0.288 | 3.18 | 0.577 | 5.31 | 2.248 | 2.97 | 0.161 |

As may be seen from the results of Table 2, full strength extract solutions from lentil, chickpea and split peas were clear to slightly hazy. Acidification without dilution increased the haze level in the samples. Dilution of the filtered extract with an equal volume of water resulted in notable precipitation and a corresponding increase in the A600 value. Acidification of the diluted solution largely re-solubilized the precipitate and resulted in a clear solution for lentils and chickpeas and a slightly hazy solution for the yellow and green split peas.

Example 2

This Example contains an evaluation of the clarity of acidified, diluted or undiluted green split pea extracts with water and sodium chloride replacing the calcium chloride solution of Example 1 as the extraction solution.

Dry green split peas were purchased in whole form and ground to a fine powder using a KitchenAid mixer grinder attachment. The extent of grinding was not controlled by time or particle size. Ground material (10 g) was extracted with 0.15M NaCl (100 ml) or RO water (100 ml) for 30 minutes on a magnetic stirrer at room temperature. The extract was separated from the spent material by centrifugation at 10,200 g for 10 minutes and then further clarified by filtration with a 0.45 μm pore size syringe filter. The clarity of the filtrates at full strength and diluted with 1 volume of RO water was determined by measuring the absorbance at 600 nm. The full strength and diluted solutions were then adjusted to pH 3 with HCl and the A600 measured again.

Clarity of the full strength and diluted extract samples before and after acidification are shown in Table 3.

TABLE 3

Effect of acidification on clarity of diluted and undiluted extract samples - water and sodium chloride extractions

| | undiluted | | | | diluted | | | |
|---|---|---|---|---|---|---|---|---|
| extraction solution | initial pH | initial A600 | final pH | final A600 | initial pH | initial A600 | final pH | final A600 |
| water | 6.56 | 0.113 | 3.14 | >3.0 | 6.62 | 0.050 | 3.00 | 2.647 |
| 0.15M NaCl | 6.19 | 0.021 | 2.96 | >3.0 | 6.28 | 0.870 | 2.87 | 2.851 |

As may be seen from the results in Table 3, extracts prepared with water or sodium chloride solution were very cloudy when acidified regardless of whether a dilution step was employed.

Example 3

This Example evaluates the protein extractability of several types of dry beans and the effect of acidification on the clarity of protein solutions resulting from the extraction step.

Pinto beans, small white beans, small red beans, romano beans, great northern beans and lima beans were purchased in whole, dry form and ground using a Bamix chopper until in the form of a relatively fine powder. The extent of grinding was not controlled by time or particle size. Black bean flour was also purchased. Ground material or flour (10 g) was extracted with 0.15M $CaCl_2$ (100 ml) for 30 minutes on a magnetic stirrer at room temperature. The extract was separated from the spent material by centrifugation at 10,200 g for 10 minutes and then further clarified by filtration with a 0.45 μm pore size syringe filter. The ground starting material or flour and the clarified extract were tested for protein content using a Leco FP 528 Nitrogen Determinator. The clarity of the extract at full strength and diluted with 1 volume of RO water was determined by measuring the absorbance at 600 nm. The full strength and diluted solutions were then adjusted to pH 3 with HCl and the A600 measured again.

The protein contents and apparent extractabilities determined for each type of dry bean are shown in Table 4.

TABLE 4

Protein content and apparent extractability of various dry beans

| type of bean | protein content (%) | apparent extractability (%) |
|---|---|---|
| black bean | 24.00 | 77.9 |
| pinto bean | 21.45 | 66.2 |
| small white bean | 24.41 | 63.5 |
| small red bean | 20.18 | 76.8 |
| romano bean | 18.07 | 86.9 |
| great northern bean | 21.77 | 85.9 |
| lima bean | 21.43 | 71.9 |

As may be seen from the results in Table 4, the protein in all of the types of beans was readily extracted.

Clarity of the full strength and diluted extract samples before and after acidification are shown in Table 5.

TABLE 5

Effect of acidification on clarity of diluted and undiluted extract samples - calcium chloride extraction

| | undiluted | | | | diluted 1 + 1 | | | |
|---|---|---|---|---|---|---|---|---|
| sample | initial pH | initial A600 | final pH | final A600 | initial pH | initial A600 | final pH | final A600 |
| black bean | 4.69 | 0.100 | 2.99 | 0.154 | 4.76 | 0.025 | 3.15 | 0.031 |
| pinto bean | 5.08 | 0.014 | 3.02 | 0.072 | 5.34 | 0.003 | 3.00 | 0.017 |
| small white bean | 5.08 | 0.026 | 3.03 | 0.092 | 5.23 | 0.022 | 3.03 | 0.019 |
| small red bean | 5.06 | 0.028 | 3.07 | 0.093 | 5.33 | 0.014 | 2.97 | 0.021 |
| romano bean | 4.96 | n.d. | 3.07 | 0.023 | 5.21 | 0.005 | 2.86 | 0.008 |
| gr. northern bean | 4.93 | 0.026 | 3.10 | 0.045 | 5.16 | 0.008 | 3.11 | 0.013 |
| lima bean | 5.13 | n.d. | 3.07 | 0.089 | 5.37 | 0.020 | 3.04 | 0.013 | n.d. = not determined

As may be seen from the results of Table 5, full strength extract solutions from all of the beans were quite clear. Acidification without dilution slightly increased the haze level in the samples but they remained quite clear. Dilution of the filtered extract with an equal volume of water did not result in the formation of any precipitate. This is in contrast to the precipitation seen upon dilution for the pulses tested in Example 1. The diluted bean protein solutions stayed clear when acidified.

Example 4

This Example contains an evaluation of the clarity of acidified, diluted or undiluted small white bean extracts with water and sodium chloride replacing the calcium chloride solution of Example 3 as the extraction solution.

Dry small white beans were purchased in whole form and ground to a fine powder using a Bamix chopper. The extent of grinding was not controlled by time or particle size. Ground material (10 g) was extracted with 0.15M NaCl (100 ml) or RO water (100 ml) for 30 minutes on a magnetic stirrer at room temperature. The extract was separated from the spent material by centrifugation at 10,200 g for 10 minutes and then further clarified by filtration with a 0.45 µm pore size syringe filter. The protein content of the filtrates was determined using a Leco FP528 Nitrogen Determinator. The clarity of the extracts at full strength and diluted with 1 volume of RO water was determined by measuring the absorbance at 600 nm. The full strength and diluted solutions were then adjusted to pH 3 with HCl and the A600 measured again.

Extraction with water and sodium chloride solution provided apparent extractabilities of 45.9% and 61.5% respectively. Clarity of the full strength and diluted extract samples before and after acidification are shown in Table 6.

TABLE 6

Effect of acidification on clarity of diluted and undiluted extract samples - water and sodium chloride extractions

| | undiluted | | | | diluted | | | |
|---|---|---|---|---|---|---|---|---|
| extraction solution | initial pH | initial A600 | final pH | final A600 | initial pH | initial A600 | final pH | final A600 |
| water | 6.48 | 0.079 | 2.95 | >3.0 | 6.51 | 0.051 | 3.03 | 2.771 |
| 0.15M NaCl | 6.13 | 0.116 | 3.01 | >3.0 | 6.22 | 0.212 | 3.02 | >3.0 |

As may be seen from the results in Table 6, extracts prepared with water or sodium chloride solution were very cloudy when acidified regardless of whether a dilution step was employed.

Example 5

This Example illustrates the production of green pea protein isolate at benchtop scale.

180 g of dry green split peas were finely ground using a KitchenAid mixer grinder attachment. 150 g of finely ground green split pea flour was combined with 1,000 ml of 0.15 M $CaCl_2$ solution at ambient temperature and agitated for 30 minutes to provide an aqueous protein solution. The residual solids were removed and the resulting protein solution was clarified by centrifugation and filtration to produce a filtered protein solution having a protein content of 1.83% by weight. 655 ml of the filtered protein solution was added to 655 ml of RO water and the pH of the sample lowered to 3.03 with HCl solution.

The diluted and acidified protein extract solution was reduced in volume from 1250 ml to 99 ml by concentration on a PES membrane having a molecular weight cutoff of 10,000 Daltons. An aliquot of 96 ml of concentrated protein solution was then diafiltered on the same membrane with 480 ml of RO water. The resulting acidified, diafiltered, concentrated protein solution had a protein content of 7.97% by weight and represented a yield of 65.5 wt % of the initial filtered protein solution that was further processed. The acidified, diafiltered, concentrated protein solution was dried to yield a product found to have a protein content of 95.69% (N×6.25) d.b. The product was termed GP701-01 protein isolate.

8.30 g of GP701-01 was produced. A solution of GP701-01 was prepared by dissolving sufficient protein powder to provide 0.48 g protein in 15 ml RO water and the pH measured with a pH meter and the color and clarity assessed using a HunterLab Color Quest XE instrument operated in transmission mode. The results are shown in the following Table 7.

TABLE 7 pH and HunterLab scores for solution of GP701-01

| sample | pH | L* | a* | b* | haze |
|---|---|---|---|---|---|
| GP701-01 | 3.17 | 89.46 | 1.10 | 14.98 | 63.3 |

As may be seen from the results in Table 7, the solution of GP701-01 was translucent and had a light color.

The solution of GP701-01 was heated to 95° C., held at this temperature for 30 seconds and then immediately cooled to room temperature in an ice bath. The clarity was re-measured with the HunterLab instrument and the results are shown in Table 8.

TABLE 8

HunterLab scores for solution of GP701-01 after heat treatment

| sample | L* | a* | b* | haze |
|---|---|---|---|---|
| GP701-01 | 95.56 | −0.06 | 9.65 | 47.0 |

As may be seen from the results in Table 8, heat treatment was found to improve the lightness and reduce the haze level of the solution while making it greener and less yellow.

Although the level of haze in the solution was reduced, the protein solution was still translucent rather than transparent.

Example 6

This Example illustrates the production of green pea protein isolate at benchtop scale but with the filtration step moved to after dilution and acidification of the extract.

180 g of dry green split peas were finely ground using a KitchenAid mixer grinder attachment. 150 g of finely ground green split pea flour was combined with 1,000 ml of 0.15 M $CaCl_2$ solution at ambient temperature and agitated for 30 minutes to provide an aqueous protein solution. The residual solids were removed by centrifugation to produce a centrate having a protein content of 2.49% by weight. 800 ml of centrate was added to 800 ml of water and the pH of the sample lowered to 3.00 with diluted HCl. The diluted and acidified centrate was further clarified by filtration to provide a clear protein solution with a protein content of 1.26% by weight. By filtering the solution after dilution and acidification, the A600 of the solution before membrane processing in this trial was 0.012, compared to 0.093 for the diluted and acidified filtrate in Example 5.

The filtered protein solution was reduced in volume from 1292 ml to 157 ml by concentration on a PES membrane having a molecular weight cutoff of 10,000 Daltons. An aliquot of 120 ml of concentrated protein solution was then diafiltered on the same membrane with 600 ml of RO water. The resulting acidified, diafiltered, concentrated protein solution had a protein content of 7.70% by weight and represented a yield of 42.5 wt % of the initial centrate that was further processed. The acidified, diafiltered, concentrated protein solution was dried to yield a product found to have a protein content of 94.23% (N×6.25) d.b. The product was termed GP701-02 protein isolate.

8.55 g of GP701-02 was produced. A solution of GP701-02 was prepared by dissolving sufficient protein powder to provide 0.48 g protein in 15 ml of RO water and the pH measured with a pH meter and the color and clarity assessed using a HunterLab Color Quest XE instrument operated in transmission mode. The results are shown in the following Table 9.

TABLE 9 pH and HunterLab scores for solution of GP701-02

| sample | pH | L* | a* | b* | haze |
|---|---|---|---|---|---|
| GP701-02 | 3.23 | 90.78 | 0.77 | 14.00 | 47.2 |

As may be seen from the results in Table 9, the GP701-02 solution was translucent and had a light color. The level of haze was lower than that determined for the solution of GP701-01 in Example 5.

The solution of GP701-02 was heated to 95° C., held at this temperature for seconds and then immediately cooled to room temperature in an ice bath. The clarity was then re-measured with the HunterLab and the result is shown in Table 10 below.

TABLE 10

HunterLab scores for solution of GP701-02 after heat treatment

| sample | L* | a* | b* | haze |
|---|---|---|---|---|
| GP701-02 | 96.24 | −0.48 | 9.74 | 2.2 |

As may be seen from the results in Table 10, heat treatment of the GP701-02 solution resulted in an extremely clear solution.

Example 7

This Example illustrates the production of small white bean protein isolate at benchtop scale.

About 150 g of small white beans were finely ground using a KitchenAid mixer grinder attachment. 120 g of finely ground small white bean flour was combined with 1,000 ml of 0.15 M $CaCl_2$ solution at ambient temperature and agitated for 30 minutes to provide an aqueous protein solution. The residual solids were removed and the resulting protein solution was clarified by centrifugation and filtration to produce a filtered protein solution having a protein content of 2.02% by weight. 600 ml of the filtered protein solution was added to 600 ml of RO water and the pH of the sample lowered to 3.01 with diluted HCl. Some wispy particulates were visible in the sample after the pH adjustment and these were removed by passing the sample through 25 μm pore size filter paper.

A sample of the diluted and acidified protein extract solution was then reduced in volume from 1110 ml to 82 ml by concentration on a PES membrane having a molecular weight cutoff of 10,000 Daltons. An aliquot of 79 ml of the retentate was then diafiltered on the same membrane with 395 ml of RO water. The resulting acidified, diafiltered, concentrated protein solution had a protein content of 10.37% by weight and represented a yield of 67.6 wt % of the initial filtered protein solution that was further processed. The acidified, diafiltered, concentrated protein solution was dried to yield a product found to have a protein content of 93.75% (N×6.25) d.b. The product was termed SWB701 protein isolate.

8.26 g of SWB701 was produced. A solution of SWB701 was prepared by dissolving sufficient protein powder to provide 0.48 g protein in 15 ml RO water and the pH measured with a pH meter and the color and clarity assessed using a HunterLab Color Quest XE instrument operated in transmission mode. The results are shown in the following Table 11.

TABLE 11 pH and HunterLab scores for solution of SWB701

| sample | pH | L* | a* | b* | haze |
|---|---|---|---|---|---|
| SWB701 | 3.09 | 97.42 | 0.22 | 5.29 | 73.2 |

As may be seen from the results in Table 11, the solution of SWB701 was translucent and had a light color.

The solution of SWB701 was heated to 95° C., held at this temperature for 30 seconds and then immediately cooled to room temperature in an ice bath. The clarity was re-measured with the HunterLab instrument and the results are shown in Table 12.

TABLE 12

HunterLab scores for solution of SWB701 after heat treatment

| sample | L* | a* | b* | haze |
|---|---|---|---|---|
| SWB701 | 98.57 | −0.17 | 4.05 | 50.0 |

As may be seen from the results in Table 12, heat treatment was found to improve the lightness and reduce the haze level of the solution while making it greener and less yellow. Although the level of haze in the solution was reduced, the protein solution was still translucent rather than transparent.

Example 8

This Example contains an evaluation of the solubility in water of the GP701-02 produced by the method of Example 6 and the SWB701 produced by the method of Example 7. Solubility was tested using a modified version of the procedure of Morr et al., J. Food Sci. 50:1715-1718.

Sufficient protein powder to supply 0.5 g of protein was weighed into a beaker and then approximately 45 ml of reverse osmosis (RO) purified water was added. The contents of the beaker were slowly stirred for 60 minutes using a magnetic stirrer. The pH was determined immediately after dispersing the protein and was adjusted to the appropriate level (2, 3, 4, 5, 6 or 7) with diluted NaOH or HCl. A sample was also prepared at natural pH. For the pH adjusted samples, the pH was measured and corrected periodically during the 60 minutes stirring. After the 60 minutes of stirring, the samples were made up to 50 ml total volume with RO water, yielding a 1% w/v protein dispersion. The protein content of the dispersions was measured using a Leco FP528 Nitrogen Determinator. Aliquots of the dispersions were then centrifuged at 7,800 g for 10 minutes, which sedimented insoluble material. The protein content of the supernatant was then determined by Leco analysis.

The solubility of the protein was then calculated using the following equation:

Solubility (%)=(% protein in supernatant/% protein in initial dispersion)×100

The natural pH values of the protein isolates produced in Examples 6 and 7 are shown in the following Table 13:

TABLE 13

Natural pH of samples prepared in water at 1% w/v protein

| sample | Natural pH |
|---|---|
| GP701-02 | 3.23 |
| SWB701 | 3.09 |

The solubility results obtained are set forth in the following Table 14:

TABLE 14

Solubility of products at different pH values

| | Solubility (%) | | | | | | |
|---|---|---|---|---|---|---|---|
| sample | pH 2 | pH 3 | pH 4 | pH 5 | pH 6 | pH 7 | Nat. pH |
| GP701-02 | 100 | 100 | 100 | 31.1 | 35.7 | 37.8 | 100 |
| SWB701 | 95.2 | 95.3 | 100 | 88.8 | 55.4 | 77.5 | 94.0 |

As can be seen from the results of Table 14, both of the 701 products were extremely soluble over the pH range 2 to 4.

Example 9

This Example contains an evaluation of the clarity in water of the GP701-02 produced by the method of Example 6 and the SWB701 produced by the method of Example 7.

The clarity of the 1% w/v protein dispersions prepared as described in Example 8 was assessed by analyzing the samples on a HunterLab ColorQuest XE instrument operated in transmission mode to provide a percentage haze reading. A lower score indicated greater clarity.

The clarity results are set forth in the following Table 15:

TABLE 15

Clarity of solutions at different pH values as assessed by HunterLab analysis

| | HunterLab haze reading (%) | | | | | | |
|---|---|---|---|---|---|---|---|
| sample | pH 2 | pH 3 | pH 4 | pH 5 | pH 6 | pH 7 | Nat. pH |
| GP701-02 | 11.9 | 16.3 | 17.4 | 91.8 | 92.1 | 92.0 | 14.0 |
| SWB701 | 0.0 | 38.0 | 64.6 | 91.7 | 92.4 | 82.9 | 43.9 |

As can be seen from the results of Table 15, the solutions of GP701-02 were substantially clear or slightly hazy in the pH range 2 to 4. The solutions of GP701-02 were cloudy at the higher pH values where the solubility was reduced. The solution of SWB701 had no detectable haze at pH 2, but was noticeably hazier as the pH increased. Note that the protein solubility was still very high in the pH range 3 to 4 even though the solutions were not clear.

Example 10

This Example illustrates the production of black bean protein product at benchtop scale.

50 g of black bean flour was combined with 500 ml of 0.15 M $CaCl_2$ solution at ambient temperature and agitated for 30 minutes to provide an aqueous protein solution. The residual solids were removed and the resulting protein solution was clarified by centrifugation and filtration to produce a filtered protein solution having a protein content of 1.18% by weight. 450 ml of the filtered protein solution was added to 450 ml of RO water and the pH of the sample lowered to 3.09 with diluted HCl.

The diluted and acidified protein extract solution was then reduced in volume from 900 ml to 50 ml by concentration on a PES membrane having a molecular weight cutoff of 10,000 Daltons. An aliquot of 40 ml of the retentate was then diafiltered on the same membrane with 200 ml of RO water. The resulting acidified, diafiltered, concentrated protein solution had a protein content of 6.23% by weight and represented a yield of approximately 46.9 wt % of the initial filtered protein solution that was further processed. The acidified, diafiltered, concentrated protein solution was dried to yield a product found to have a protein content of 86.33% (N×6.25) d.b. The product was termed BB701.

2.19 g of BB701 was produced. A solution of BB701 was prepared by dissolving sufficient protein powder to provide 0.48 g protein in 15 ml of RO water and the pH measured with a pH meter and the color and clarity assessed using a HunterLab Color Quest XE instrument operated in transmission mode. The results are shown in the following Table 16.

TABLE 16 pH and HunterLab scores for solution of BB701

| sample | pH | L* | a* | b* | haze |
|---|---|---|---|---|---|
| BB701 | 3.14 | 95.20 | 0.88 | 8.22 | 54.6 |

As may be seen from the results in Table 16, the solution of BB701 was translucent and had a light color.

The solution of BB701 was heated to 95° C., held at this temperature for 30 seconds and then immediately cooled to room temperature in an ice bath. The clarity was re-measured with the HunterLab instrument and the results are shown in Table 17

TABLE 17

HunterLab scores for solution of BB701 after heat treatment

| sample | L* | a* | b* | haze |
|---|---|---|---|---|
| BB701 | 95.89 | 0.54 | 7.81 | 25.2 |

As may be seen from the results in Table 17, heat treatment was found to improve the lightness and reduce the haze level of the solution while making it less red and less yellow. Although the level of haze in the solution was reduced, the protein solution was still hazy rather than transparent.

Example 11

This Example illustrates the production of yellow pea protein isolate at pilot scale.

20 kg of yellow split pea flour was combined with 200 L of 0.15 M $CaCl_2$ solution at ambient temperature and agitated for 30 minutes to provide an aqueous protein solution. The residual solids were removed by centrifugation to produce a centrate having a protein content of 1.53% by weight. 180.4 L of centrate was added to 231.1 L of RO water and the pH of the sample lowered to about 3 with diluted HCl. The diluted and acidified centrate was further clarified by filtration to provide a clear protein solution with a protein content of 0.57% by weight and having a pH of 2.93.

The filtered protein solution was reduced in volume from 431 L to 28 L by concentration on a PES membrane, having a molecular weight cutoff of 100,000 Daltons, operated at a temperature of about 30° C. At this point the acidified protein solution, with a protein content of 6.35% by weight, was diafiltered with 252 L of RO water, with the diafiltration operation conducted at about 30° C. The resulting diafiltered solution was then further concentrated to provide 21 kg of acidified, diafiltered, concentrated protein solution with a protein content of 7.62% by weight, which represented a yield of 58.0 wt % of the initial centrate that was further processed. The acidified, diafiltered, concentrated protein solution was dried to yield a product found to have a protein content of 103.27 wt % (N×6.25) d.b. The product was termed YP01-D11-11A YP701 protein isolate.

Example 12

This Example contains an evaluation of the protein and phytic acid content as well as the trypsin inhibitor activity of the yellow pea protein isolate produced by the method of Example 11 and a commercial yellow pea protein product called Propulse (Nutri-pea, Portage la Prairie, MB).

Protein content was determined by a combustion method using a LecoTruSpec N Nitrogen Determinator. Phytic acid content was determined using the method of Latta and Eskin (J. Agric. Food Chem., 28: 1313-1315). Trypsin inhibitor activity (TIA) was determined using AOCS method Ba 12-75 for the commercial protein sample and a modified version of this method for the YP701 product, which has a lower pH when rehydrated.

The results obtained are set forth in the following Table 18:

TABLE 18

Protein content, phytic acid content and trypsin inhibitor activity of protein products

| Batch | Product | % protein (N x 6.25) d.b. | % phytic acid d.b. | TIA (TIU/mg protein (N x 6.25)) |
|---|---|---|---|---|
| YP01-D11-11A | YP701 | 103.27 | 0.27 | 4.6 |
| | Propulse | 82.33 | 2.72 | 3.3 |

As may be seen from the results presented in Table 18, the YP701 was very high in protein and low in phytic acid compared to the commercial product. The trypsin inhibitor activity in both products was very low.

Example 13

This Example contains an evaluation of the dry color and color in solution of the yellow pea protein isolate produced by the method of Example 11 and a commercial yellow pea protein product called Propulse (Nutri-pea, Portage la Prairie, MB).

The color of the dry powders was assessed using a HunterLab ColorQuest XE instrument in reflectance mode. The color values are set forth in the following Table 19:

TABLE 19

HunterLab scores for dry protein products

| Sample | L* | a* | b* |
|---|---|---|---|
| YP01-D11-11A YP701 | 86.27 | 2.21 | 9.73 |
| Propulse | 82.39 | 3.29 | 20.94 |

As may be seen from Table 19, the YP01-D11-11A YP701 powder was lighter, less red and less yellow in color compared to the commercial yellow pea protein product.

Solutions of the yellow pea protein products were prepared by dissolving sufficient protein powder to supply 0.48 g of protein in 15 ml of RO water. The pH of the solutions was measured with a pH meter and the color and clarity assessed using a HunterLab Color Quest XE instrument operated in transmission mode. Hydrochloric acid solution was added to the Propulse sample to lower the pH to 3 and then the measurement repeated. The results are shown in the following Table 20.

TABLE 20 pH and HunterLab scores for solutions of yellow pea protein products

| sample | pH | L* | a* | b* | haze |
|---|---|---|---|---|---|
| YP01-D11-11A YP701 | 3.45 | 93.97 | 0.54 | 12.70 | 5.0 |
| Propulse | 6.15 | 35.33 | 12.61 | 48.79 | 96.6 |
| Propulse (pH adjusted) | 3.00 | 37.83 | 11.55 | 47.87 | 96.9 |

As may be seen from the results in Table 20, the YP01-D11-11A YP701 solution was transparent while the Propulse solution was very cloudy regardless of pH. The YP01-D11-

11A YP701 solution was also much lighter, less red and less yellow than the Propulse solution regardless of its pH.

Example 14

This Example contains an evaluation of the heat stability in water of the yellow pea protein isolate produced by the method of Example 11 and a commercial yellow pea protein product called Propulse (Nutri-pea, Portage la Prairie, MB).

Solutions of the yellow pea protein products were prepared by dissolving sufficient protein powder to supply 1.6 g of protein in 80 ml of RO water. The natural pH of the solutions was determined with a pH meter. The samples were each split into two portions and the pH of one portion was lowered to 3.00 with HCl solution. The clarity of the control and pH adjusted solutions was assessed by haze measurement with the HunterLab Color Quest XE instrument operated in transmission mode. The solutions were then heated to 95° C., held at this temperature for 30 seconds and then immediately cooled to room temperature in an ice bath. The clarity of the heat treated solutions was then measured again.

The clarity of the protein solutions before and after heating is set forth in the following Table 21:

TABLE 21

Effect of heat treatment on clarity of 2% w/v protein solutions of yellow pea protein products

| sample | pH | haze before heat treatment (%) | haze after heat treatment (%) |
|---|---|---|---|
| YP01-D11-11A YP701 | 3.70 | 3.6 | 1.4 |
| YP01-D11-11A YP701 (pH adjusted) | 3.00 | 2.8 | 1.3 |
| Propulse | 6.24 | 96.1 | 96.4 |
| Propulse (pH adjusted) | 3.00 | 96.6 | 96.6 |

As can be seen from the results in Table 21, the solutions of YP01-D11-11A YP701 were transparent before and after heating at both pH levels. The solutions of Propulse were highly cloudy before and after heating at both pH levels.

Example 15

This Example contains an evaluation of the solubility in water of the yellow pea protein isolate produced by the method of Example 11 and a commercial yellow pea protein product called Propulse (Nutri-pea, Portage la Prairie, MB). Solubility was tested based on protein solubility (termed protein method, a modified version of the procedure of Morr et al., J. Food Sci. 50:1715-1718) and total product solubility (termed pellet method).

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3, 4, 5, 6 or 7) with diluted NaOH or HCl. A sample was also prepared at natural pH. For the pH adjusted samples, the pH was measured and corrected periodically during the 60 minutes stirring. After the 60 minutes of stirring, the samples were made up to 50 ml total volume with RO water, yielding a 1% w/v protein dispersion. The protein content of the dispersions was measured using a Leco TruSpec N Nitrogen Determinator. Aliquots (20 ml) of the dispersions were then transferred to pre-weighed centrifuge tubes that had been dried overnight in a 100° C. oven then cooled in a desiccator and the tubes capped. The samples were centrifuged at 7,800 g for 10 minutes, which sedimented insoluble material and yielded a clear supernatant. The protein content of the supernatant was measured by Leco analysis and then the supernatant and the tube lids were discarded and the pellet material dried overnight in an oven set at 100° C. The next morning the tubes were transferred to a desiccator and allowed to cool. The weight of dry pellet material was recorded. The dry weight of the initial protein powder was calculated by multiplying the weight of powder used by a factor of ((100−moisture content of the powder (%))/100). Solubility of the product was then calculated two different ways:

Solubility(protein method)(%)=(% protein in supernatant/% protein in initial dispersion)×100     1)

Solubility(pellet method)(%)=(1−(weight dry insoluble pellet material/((weight of 20 ml of dispersion/weight of 50 ml of dispersion)×initial weight dry protein powder)))×100     2)

The natural pH values of the protein isolate produced in Example 11 and the commercial yellow pea protein product in water (1% protein) are shown in Table 22:

TABLE 22

Natural pH of YP01-D11-11A YP701 and Propulse solutions prepared in water at 1% protein

| Batch | Product | Natural pH |
|---|---|---|
| YP01-D11-11A | YP701 | 3.56 |
| | Propulse | 6.15 |

The solubility results obtained are set forth in the following Tables 23 and 24:

TABLE 23

Solubility of products at different pH values based on protein method

| | | Solubility (protein method) (%) | | | | | | |
|---|---|---|---|---|---|---|---|---|
| Batch | Product | pH 2 | pH 3 | pH 4 | pH 5 | pH 6 | pH 7 | Nat. pH |
| YP01-D11-11A | YP701 | 98.2 | 99.1 | 99.5 | 50.9 | 20.4 | 39.3 | 100 |
| | Propulse | 14.9 | 3.6 | 2.6 | 5.3 | 10.3 | 7.0 | 8.0 |

TABLE 24

Solubility of products at different pH values based on pellet method

| | | Solubility (pellet method) (%) | | | | | | |
|---|---|---|---|---|---|---|---|---|
| Batch | Product | pH 2 | pH 3 | pH 4 | pH 5 | pH 6 | pH 7 | Nat. pH |
| YP01-D11-11A | YP701 | 99.6 | 99.3 | 99.1 | 74.7 | 34.7 | 39.1 | 99.0 |
| | Propulse | 15.5 | 14.7 | 11.6 | 12.1 | 16.4 | 18.0 | 16.5 |

As can be seen from the results presented in Table 23 and 24, the YP01-D11-11A YP701 was highly soluble in the pH range of 2 to 4 and less soluble at higher pH values. The Propulse was very poorly soluble at all pH values tested.

Example 16

This Example contains an evaluation of the clarity in water of the yellow pea protein isolate produced by the method of Example 11 and a commercial yellow pea protein product called Propulse (Nutri-pea, Portage la Prairie, MB).

The clarity of the 1% w/v protein solutions prepared as described in Example 15 was assessed by measuring the absorbance at 600 nm, with a lower absorbance score indicating greater clarity. Analysis of the samples on a HunterLab ColorQuest XE instrument in transmission mode also provided a percentage haze reading, another measure of clarity.

The clarity results are set forth in the following Tables 25 and 26:

TABLE 25

Clarity of protein solutions at different pH values as assessed by A600

| | | A600 | | | | | | |
|---|---|---|---|---|---|---|---|---|
| Batch | Product | pH 2 | pH 3 | pH 4 | pH 5 | pH 6 | pH 7 | Nat. pH |
| YP01-D11-11A | YP701 | 0.012 | 0.015 | 0.024 | 1.962 | 2.829 | 2.557 | 0.021 |
| | Propulse | 2.576 | 2.579 | 2.693 | 2.685 | 2.588 | 2.560 | 2.590 |

TABLE 26

Clarity of protein solutions at different pH values as assessed by HunterLab haze analysis

| | | HunterLab haze reading (%) | | | | | | |
|---|---|---|---|---|---|---|---|---|
| Batch | Product | pH 2 | pH 3 | pH 4 | pH 5 | pH 6 | pH 7 | Nat. pH |
| YP01-D11-11A | YP701 | 0.0 | 0.1 | 1.1 | 95.9 | 96.7 | 96.4 | 0.7 |
| | Propulse | 96.2 | 96.3 | 96.7 | 96.7 | 96.2 | 96.4 | 96.4 |

As can be seen from the results of Tables 25 and 26, the solutions of YP01-D11-11A YP701 were transparent in the range of pH 2 to 4 but very cloudy at higher pH values. The solutions of Propulse were very cloudy regardless of pH.

Example 17

This Example contains an evaluation of the solubility in a soft drink (Sprite) and sports drink (Orange Gatorade) of the yellow pea protein isolate produced by the method of Example 11 and a commercial yellow pea protein product called Propulse (Nutri-pea, Portage la Prairie, MB). The solubility was determined with the protein added to the beverages with no pH correction and again with the pH of the protein fortified beverages adjusted to the level of the original beverages.

When the solubility was assessed with no pH correction, a sufficient amount of protein powder to supply 1 g of protein was weighed into a beaker and a small amount of beverage was added and stirred until a smooth paste formed. Additional beverage was added to bring the volume to 50 ml, and then the solutions were stirred slowly on a magnetic stirrer for 60 minutes to yield a 2% protein w/v dispersion. The protein content of the samples was analyzed using a Leco TruSpec N Nitrogen Determinator then an aliquot of the protein containing beverages was centrifuged at 7,800 g for 10 minutes and the protein content of the supernatant measured.

Solubility (%)=(% protein in supernatant/% protein in initial dispersion)×100.

When the solubility was assessed with pH correction, the pH of the soft drink (Sprite) (3.42) and sports drink (Orange Gatorade) (3.11) without protein was measured. A sufficient amount of protein powder to supply 1 g of protein was weighed into a beaker and a small amount of beverage was added and stirred until a smooth paste formed. Additional beverage was added to bring the volume to approximately 45 ml, and then the solutions were stirred slowly on a magnetic stirrer for 60 minutes. The pH of the protein containing beverages was determined immediately after dispersing the protein and was adjusted to the original no-protein pH with HCl or NaOH as necessary. The pH was measured and corrected periodically during the 60 minutes stirring. After the 60 minutes of stirring, the total volume of each solution was brought to 50 ml with additional beverage, yielding a 2% protein w/v dispersion. The protein content of the samples was analyzed using a Leco TruSpec N Nitrogen Determinator then an aliquot of the protein containing beverages was centrifuged at 7,800 g for 10 minutes and the protein content of the supernatant measured.

Solubility (%)=(% protein in supernatant/% protein in initial dispersion)×100

The results obtained are set forth in the following Table 27:

TABLE 27

Solubility of yellow pea protein products in Sprite and Orange Gatorade

| | | no pH correction | | pH correction | |
|---|---|---|---|---|---|
| Batch | Product | Solubility (%) in Sprite | Solubility (%) in Orange Gatorade | Solubility (%) in Sprite | Solubility (%) in Orange Gatorade |
| YP01-D11-11A | YP701 | 98.1 | 100 | 96.6 | 100 |
| | Propulse | 3.2 | 4.6 | 5.6 | 7.4 |

As can be seen from the results of Table 27, the YP01-D11-11A YP701 was highly soluble in the Sprite and the Orange Gatorade. As the YP701 is an acidified product, its addition did not significantly alter the pH of the beverages. The Propulse was very poorly soluble in the beverages tested. Addition of Propulse increased the pH of the drinks but the solubility of the protein was not improved by lowering the pH of the drink back to its original no-protein value.

Example 18

This Example contains an evaluation of the clarity in a soft drink and sports drink of the yellow pea protein isolate produced by the method of Example 11 and a commercial yellow pea protein product called Propulse (Nutri-pea, Portage la Prairie, MB).

The clarity of the 2% w/v protein dispersions prepared in soft drink (Sprite) and sports drink (Orange Gatorade) in Example 17 were assessed using the A600 and HunterLab haze methods described in Example 16.

The results obtained are set forth in the following Tables 28 and 29:

TABLE 28

A600 readings for yellow pea protein products in Sprite and Orange Gatorade

| | | no pH correction | | pH correction | |
|---|---|---|---|---|---|
| Batch | Product | A600 in Sprite | A600 in Orange Gatorade | A600 in Sprite | A600 in Orange Gatorade |
| no protein | | 0.007 | 0.450 | 0.007 | 0.450 |
| YP01-D11-11A | YP701 | 0.048 | 0.338 | 0.043 | 0.345 |
| | Propulse | 2.800 | 2.834 | 2.827 | 2.793 |

TABLE 29

HunterLab haze readings for yellow pea protein products in Sprite and Orange Gatorade

| | | no pH correction | | pH correction | |
|---|---|---|---|---|---|
| Batch | Product | Haze (%) in Sprite | Haze (%) in Orange Gatorade | Haze (%) in Sprite | Haze (%) in Orange Gatorade |
| no protein | | 0.0 | 78.6 | 0.0 | 78.6 |
| YP01-D11-11A | YP701 | 5.7 | 56.7 | 4.9 | 57.7 |
| | Propulse | 97.1 | 97.5 | 96.3 | 96.3 |

As can be seen from the results of Tables 28 and 29, the addition of YP01-D11-11A YP701 to the soft drink and sports drink added little or no haziness, while the addition of the Propulse made the drinks very cloudy, even when the pH was corrected.

Example 19

This Example illustrates the production of yellow pea protein isolate at pilot scale.

20 kg of yellow split pea flour was combined with 200 L of 0.15 M CaCl$_2$ solution at 60° C. and agitated for 30 minutes to provide an aqueous protein solution. The residual solids were removed by centrifugation to produce a centrate having a protein content of 1.32% by weight 186.5 L of centrate was added to 225.8 L of RO water at 60° C. and the pH of the sample lowered to 3.34 with diluted HCl. The diluted and acidified centrate was further clarified by filtration to provide a clear protein solution with a protein content of 0.58% by weight.

The filtered protein solution was reduced in volume from 400 L to 35 L by concentration on a polyethersulfone membrane, having a molecular weight cutoff of 100,000 Daltons, operated at a temperature of about 58° C. At this point the acidified protein solution, with a protein content of 4.94 wt %, was diafiltered with 350 L of RO water, with the diafiltration operation conducted at about 60° C. The resulting diafiltered solution was then further concentrated to provide 21.52 kg of acidified, diafiltered, concentrated protein solution with a protein content of 7.54% by weight, which represented a yield of 65.9 wt % of the initial centrate that was further processed. The acidified, diafiltered, concentrated protein solution was dried to yield a product found to have a protein content of 103.19 wt % (N×6.25) d.b. The product was termed YP01-E19-11A YP701 protein isolate.

Example 20

This Example illustrates a comparison of the flavor of the YP701, prepared as described in Example 19, with that of a commercial yellow pea protein product called Nutralys S85F (Roquette America, Inc. Keokuk, Iowa), with the evaluation done at low pH.

Samples were prepared for sensory evaluation by dissolving sufficient protein powder to supply 5 g of protein in 250 ml purified drinking water. The pH of the solution of YP701 was determined to be 3.78. Food grade HCl was added to the solution of Nutralys S85F to lower the pH from 7.25 to 3.78. An informal panel of seven panelists was asked to blindly compare the samples and indicate which sample had a cleaner flavour, and of which sample they preferred the flavour.

Seven out of seven panelists indicated that the YP701 had a cleaner flavour. Seven out of seven panelists preferred the flavour of the YP701.

Example 21

This Example illustrates a comparison of the flavour of the YP701, prepared as described in Example 19, with that of the commercial yellow pea protein product Nutralys S85F, with the evaluation done at near neutral pH.

Samples were prepared for sensory evaluation by dissolving sufficient protein powder to supply 5 g of protein in 250 ml purified drinking water. The pH of the solution of Nutralys S85F was determined to be 7.32. Food grade NaOH was added to the solution of YP701 to raise the pH from 3.67 to 732. An informal panel of eight panelists was asked to blindly compare the samples and indicate which sample had a cleaner flavour, and of which sample they preferred the flavour.

Six out of eight panelists indicated that the YP701 had a cleaner flavour. Six out of eight panelists preferred the flavour of the YP701.

Example 22

This Example illustrates a comparison of the flavour of the YP701, prepared as described in Example 19, with that a commercial yellow pea protein product called Propulse (Nutri-Pea, Portage la Prairie, MB), with the evaluation done at low pH.

Samples were prepared for sensory evaluation by dissolving sufficient protein powder to supply 5 g of protein in 250 ml purified drinking water. The pH of the solution of YP701 was determined to be 3.78. Food grade HCl was added to the solution of Propulse to lower the pH from 6.17 to 3.78. An informal panel of seven panelists was asked to blindly compare the samples and indicate which sample had a cleaner flavour, and of which sample they preferred the flavour.

Six out of seven panelists indicated that the YP701 had a cleaner flavour. Seven out of seven panelists preferred the flavour of the YP701.

Example 23

This Example illustrates a comparison of the flavour of the YP701, prepared as described in Example 19, with that of the commercial yellow pea protein product called Propulse, with the evaluation done at near neutral pH.

Samples were prepared for sensory evaluation by dissolving sufficient protein powder to supply 5 g of protein in 250 ml purified drinking water. The pH of the solution of Propulse was determined to be 6.18. Food grade NaOH was added to the solution of YP701 to raise the pH from 3.78 to 6.18. An informal panel of eight panelists was asked to blindly compare the samples and indicate which sample had a cleaner flavour, and of which sample they preferred the flavour.

Seven out of eight panelists indicated that the YP701 had a cleaner flavour. Six out of eight panelists preferred the flavour of the YP701.

In the Examples which follow, certain data pertaining to the YP01-D11-11A YP701 pea protein isolate and the commercial yellow pea protein product Propulse, already presented in Examples 11 to 16, is presented a second time for convenience of comparison with other pea protein isolates and commercial yellow pea protein products.

Example 24

This Example illustrates the production of yellow pea protein isolates at pilot scale.

'a' kg of 'b' was combined with 'c' L of 'd' at 'e' and agitated for 'f' minutes. 'g' kg of calcium chloride pellets (95.5%) dissolved in 'h' L of RO water was then added and the mixture stirred for an additional 'i' minutes. The residual solids were removed by centrifugation to produce a centrate having a protein content of 'j' % by weight. 'k' L of centrate was added to 'l'L of RO water at 'm' and the pH of the sample lowered to 'n' with diluted HCl. The diluted and acidified centrate was further clarified by filtration to provide a clear protein solution with a protein content of 'o' % by weight.

The filtered protein solution was reduced in volume from 'p' L to 'q' L by concentration on a polyethersulfone membrane, having a molecular weight cutoff of 'r' Daltons, operated at a temperature of about 's' ° C. At this point the protein solution, with a protein content of 't' wt %, was diafilterd with 'u' L of RO water, with the diafiltration operation conducted at about 'v' ° C. The diafiltered protein solution was then concentrated to 'w', and then 'x' L of the sample diafiltered with an additional 'y' L of RO water, with the diafiltration operation conducted at approximately 'z' ° C. The concentrated protein solution, having a protein content of 'aa' wt % was further concentrated to a protein content of 'ab' wt %, then diluted with RO water to a protein content of 'ac' wt % to facilitate spray drying. The protein solution before spray drying, having a weight of 'ad' kg was recovered in a yield of 'ac' % of the initial centrate that was further processed. The concentrated and diafiltered protein solution was then dried to yield a product found to have a protein content of 'af' wt % (N×6.25) d.b. The product was given designation 'ag'. The parameters 'a' to 'ag' are set forth in the following Table 30.

TABLE 30

Parameters for the runs to produce YP 701

| ag | YP01-D11-11A YP701 | YP01-E19-11A YP701 | YP03-J05-11A YP701 | YP05-A18-12A YP701 | YP06-B06-12A YP701-01 | YP06-B07-12A YP701 |
|---|---|---|---|---|---|---|
| a | 20 | 20 | 30 | 70 | 70 | 70 |
| b | Yellow split pea flour | Yellow split pea flour | Yellow pea protein concentrate | Yellow split pea flour | Yellow split pea flour | Yellow split pea flour |
| c | 200 | 200 | 300 | 300 | 300 | 300 |
| d | 0.15M $CaCl_2$ | 0.15M $CaCl_2$ | 0.15M $CaCl_2$ | RO water | RO water | RO water |
| e | Ambient temperature | 60° C. | 60° C. | 30° C. | 30° C. | 30° C. |
| f | 30 | 30 | 30 | 60 | 60 | 60 |
| g | 0 | 0 | 0 | 4.52 | 4.53 | 4.53 |
| h | 0 | 0 | 0 | 10 | 10 | 10 |
| i | 0 | 0 | 0 | 30 | 15 | 15 |
| j | 1.53 | 1.32 | 3.50 | 2.92 | 3.37 | 2.86 |
| k | 180.4 | 386.5 | 254.9 | 223.3 | 210 | 220 |
| l | 231.1 | 225.8 | 346.2 | 223.0 | 137 | 143 |
| m | Ambient temperature | 60° C. | 60° C. | Ambient temperature | Ambient temperature | Ambient temperature |
| n | 2.93 | 3.34 | 3.26 | 3.04 | Approx. 3 | 3.03 |
| o | 0.63 | 0.58 | 1.62 | 1.25 | 1.45 | 1.37 |
| p | 431 | 400 | 548 | 550 | 385 | 405 |
| q | 28 | 35 | 51 | 101 | 77 | 72 |
| r | 100,000 | 100,000 | 10,000 | 10,000 | 10,000 | 10,000 |
| s | 30 | 58 | 56 | 53 | 48 | 51 |
| t | 6.35 | 4.94 | 10.03 | 4.05 | 4.82 | 5.29 |
| u | 252 | 350 | 510 | 202 | 154 | 144 |
| v | 30 | 60 | 58 | 53 | 57 | 58 |
| w | 21 kg | 21.52 kg | n/a | 34.78 kg | 30.75 L | 36 L |
| x | n/a | n/a | n/a | n/a | 20.75 | 36 |
| y | n/a | n/a | n/a | n/a | 103.75 | 180 |
| z | n/a | n/a | n/a | n/a | 58 | 58 |
| aa | 7.62 | 7.54 | 9.85 | 10.02 | 8.82 | 9.97 |
| ab | n/a | n/a | n/a | n/a | 11.75 | 12.20 |
| ac | n/a | n/a | n/a | 5.00 | 6.59 | 6.45 |
| ad | 21 | 21.52 | 52.98 | 57.9 | 33.8 | 54.66 |

TABLE 30-continued

Parameters for the runs to produce YP 701

| ag | YP01-D11-11A YP701 | YP01-E19-11A YP701 | YP03-J05-11A YP701 | YP05-A18-12A YP701 | YP06-B06-12A YP701-01 | YP06-B07-12A YP701 |
|---|---|---|---|---|---|---|
| ae | 58.0 | 65.9 | 58.5 | 44.5 | 31.5 | 56.1 |
| af | 103.27 | 103.19 | 102.62 | 101.99 | 104.64 | 102.73 |

Example 25

This Example illustrates the protein content of the commercial yellow pea protein products Propulse (Nutri-Pea, Portage la Prairie, MB), Nutralys S85F (Roquette America, Inc. Keokuk, Iowa) and Pisane C9 (Cosucra Groupe Warcoing S.A., Belgium). These protein products are among the most highly purified pea protein ingredients currently commercially available.

The protein content of the commercial samples was determined and the values are shown in Table 31.

TABLE 31

Protein content of commercial yellow pea products

| Product | % protein ((N × 6.25) d.b.) |
|---|---|
| Propulse | 82.33 |
| Nutralys S85F | 83.10 |
| Pisane C9 | 86.87 |

As may be seen from the values presented in Table 31, the protein content of the commercial yellow pea protein products was notably lower than the protein content of the yellow pea protein isolates prepared as described in Example 24.

Example 26

This Example illustrates the molecular weight profile of the yellow pea protein isolates prepared as described in Example 24 as well as the commercial yellow pea protein products.

Protein samples were analyzed by size exclusion chromatography using a Varian ProStar HPLC system equipped with a 300×7.8 mm Phenomenex S-2000 series column. The column contained hydrophilic bonded silica rigid support media, 5 micron diameter, with 145 Angstrom pore size. 0.05M NaCl, pH 3.5 containing 0.02% sodium azide was used as the mobile phase and also to dissolve dry samples. The mobile phase flow rate was 1 mL/minute and components were detected based on absorbance at 280 nm. Protein samples were mixed with mobile phase solution to a concentration of 1% w/v for pea protein products, placed on a shaker for at least 1 hour then filtered using 0.45 μm pore size filter discs. Sample injection size was 50 μL. The HPLC ProStar system automatically calculated retention times and peak areas and printed out a summary report.

Before the pea protein samples were analyzed, a standard curve was prepared using a Biorad protein standard (Biorad product #151-1901) containing proteins with known molecular weights between 17,000 Daltons (myoglobulin) and 670,000 Daltons (thyroglobulin) with Vitamin B12 added as a low molecular weight marker at 1,350 Daltons. A 0.9% w/v solution of the protein standard was prepared in the mobile phase and analyzed as described above. Based on the retention times of these molecules of known molecular weight, a regression formula was developed relating the log (MW) to the retention time in minutes.

Retention time(min)=−2.353×log(Molecular weight)+ 18.853($r^2$=0.99)

This formula was used to calculate retention times that corresponded to molecular weights of 100,000 Da, 15,000 Da, 5,000 Da and 1,000 Da. When the pea protein samples were analyzed, the peak areas lying within these retention times were used to calculate the percentage of protein ((range peak area/total protein peak area)×100) falling in a given molecular weight range. Note that the data was not corrected by protein response factor.

The molecular weight profiles of the products prepared as described in Example 24 and the commercial products are shown in Table 32.

TABLE 32

Molecular weight profile of pea protein products

| product | % >100,000 Da | % 15,000-100,000 Da | % 5,000-15,000 Da | % 1,000-5,000 Da |
|---|---|---|---|---|
| YP01-D11-11A YP701 | 77 | 16 | 4 | 3 |
| YP01-E19-11A YP701 | 89 | 10 | 1 | 0 |
| YP03-J05-11A YP701 | 85 | 11 | 2 | 2 |
| YP05-A18-12A YP701 | 80 | 13 | 3 | 3 |
| YP06-B06-12A YP701-01 | 81 | 14 | 3 | 2 |
| YP06-B07-12A YP701 | 84 | 13 | 2 | 1 |
| Propulse | 11 | 25 | 13 | 51 |
| Nutralys S85F | 4 | 25 | 7 | 64 |
| Pisane C9 | 9 | 43 | 14 | 35 |

As may be seen from the results presented in Table 32, the molecular weight profile of the yellow pea protein isolates prepared as described in Example 24 was different from the molecular weight profile of the commercial yellow pea protein products.

Example 27

This Example contains an evaluation of the phytic acid content of the yellow pea protein isolates produced as described in Example 24 as well as the commercial yellow pea protein products. Phytic acid content was determined using the method of Latta and Eskin (J. Agric. Food Chem., 28: 1313-1315).

The results obtained are set forth in the following Table 33.

TABLE 33

Phytic acid content of protein products

| Product | % phytic acid d.b. |
|---|---|
| YP01-D11-11A YP701 | 0.27 |
| YP01-E19-11A YP701 | 0.23 |

TABLE 33-continued

Phytic acid content of protein products

| Product | % phytic acid d.b. |
|---|---|
| YP03-J05-11A YP701 | 0.15 |
| YP05-A18-12A YP701 | 0.22 |
| YP06-B06-12A YP701-01 | 0.04 |
| YP06-B07-12A YP701 | 0.02 |
| Propulse | 2.72 |
| Nutralys S85F | 2.24 |
| Pisane C9 | 1.94 |

As may be seen from the results presented in Table 32, all of the pea protein isolates produced by the method of Example 24 were very low in phytic acid, having phytic acid contents much lower than the commercial yellow pea protein products.

Example 28

This Example illustrates the protein solubility at pH 2 to 4 of the yellow pea protein isolates prepared as described in Example 24 as well as the commercial yellow pea protein products. Solubility was tested by a modified version of the procedure of Morr et al., J. Food Sci., 50: 1715-1718.

Sufficient protein powder to supply 0.5 g of protein was weighed into a beaker and then a small amount of reverse osmosis (RO) purified water was added and the mixture stirred until a smooth paste formed. Additional water was then added to bring the volume to approximately 45 ml. The contents of the beaker were then slowly stirred for 60 minutes using a magnetic stirrer. The pH was determined immediately after dispersing the protein and was adjusted to the appropriate level (2, 3 or 4) with diluted NaOH or HCl. The pH was measured and corrected periodically during the 60 minutes stirring. After the 60 minutes of stirring, the samples were made up to 50 ml total volume with RO water, yielding a 1% w/v protein dispersion. The protein content of the dispersions was measured using a Leco TruSpec N Nitrogen Determinator. Aliquots of the dispersions were then centrifuged at 7,800 g for 10 minutes, which sedimented insoluble material and yielded a clear supernatant. The protein content of the supernatant was measured by Leco analysis and the solubility of the product calculated as follows:

Solubility (%)=(% protein in supernatant/% protein in initial dispersion)×100

The protein solubility results obtained are set forth in the following Table 34

TABLE 34

Solubility of products at different pH values

| | Solubility (%) | | |
|---|---|---|---|
| Product | pH 2 | pH 3 | pH 4 |
| YP01-D11-11A YP701 | 98.2 | 99.1 | 99.5 |
| YP01-E19-11A YP701 | 94.8 | 90.3 | 100 |
| YP03-J05-11A YP701 | 100 | 98.2 | 93.3 |
| YP05-A18-12A YP701 | 100 | 100 | 100 |
| YP06-B06-12A YP701-01 | 100 | 100 | 100 |
| YP06-B07-12A YP701 | 98.9 | 100 | 100 |
| Propulse | 14.9 | 3.6 | 2.6 |
| Nutralys S85F | 38.3 | 19.7 | 15.0 |
| Pisane C9 | 20.8 | 14.0 | 12.9 |

As may be seen from the results presented in Table 33, all of the pea protein isolates prepared as described in Example 24 were highly soluble in the pH range 2-4. The solubility of all of the commercial yellow pea protein products was low in the pH range 2-4.

Example 29

This Example contains an evaluation of the clarity in water of the yellow pea protein isolates prepared as described in Example 24 as well as the commercial yea pea protein products.

The clarity of the 1% w/v protein solutions prepared as described in Example 28 was assessed by measuring the absorbance at 600 nm, with a lower absorbance score indicating greater clarity. Analysis of the samples on a HunterLab ColorQuest XE instrument in transmission mode also provided a percentage haze reading, another measure of clarity.

The clarity results are set forth in the following Tables 35 and 36.

TABLE 35

Clarity of protein solutions at different pH values as assessed by A600

| | A600 | | |
|---|---|---|---|
| Product | pH 2 | pH 3 | pH 4 |
| YP01-D11-11A YP701 | 0.012 | 0.015 | 0.024 |
| YP01-E19-11A YP701 | 0.027 | 0.022 | 0.033 |
| YP03-J05-11A YP701 | 0.026 | 0.027 | 0.034 |
| YP05-A18-12A YP701 | 0.010 | 0.009 | 0.020 |
| YP06-B06-12A YP701-01 | 0.011 | 0.012 | 0.020 |
| YP06-B07-12A YP701 | 0.013 | 0.015 | 0.022 |
| Propulse | 2.576 | 2.579 | 2.693 |
| Nutralys S85F | 1.430 | 2.045 | 2.398 |
| Pisane C9 | 2.031 | 2.368 | 2.516 |

TABLE 36

Clarity of protein solutions at different pH values as assessed by HunterLab haze analysis

| | HunterLab haze reading (%) | | |
|---|---|---|---|
| Product | pH 2 | pH 3 | pH 4 |
| YP01-D11-11A YP701 | 0.0 | 0.1 | 1.1 |
| YP01-E19-11A YP701 | 2.8 | 0.9 | 4.3 |
| YP03-J05-11A YP701 | 0.3 | 0.5 | 1.6 |
| YP05-A18-12A YP701 | 0.0 | 0.0 | 0.0 |
| YP06-B06-12A YP701-01 | 0.0 | 0.0 | 0.0 |
| YP06-B07-12A YP701 | 0.0 | 0.0 | 0.0 |
| Propulse | 96.2 | 96.3 | 96.7 |
| Nutralys S85F | 96.3 | 96.8 | 96.9 |
| Pisane C9 | 97.5 | 97.6 | 97.8 |

As may be seen from the results presented in Tables 35 and 36, all of the solutions prepared from the yellow pea protein isolates prepared as described in Example 24 were very clear. The solutions prepared from the commercial yellow pea protein products were cloudy.

Example 30

This Example contains an evaluation of the heat stability in water of the yellow pea protein isolates prepared as described in Example 24 as well as the commercial yellow pea protein products.

2% w/v protein solutions were prepared in RO water. The natural pH of the solutions was determined with a pH meter. The solutions of the commercial yellow pea protein products were split into two portions and the pH of one portion was lowered to 3.00 with HCl solution. The clarity of the solutions was assessed by haze measurement with the HunterLab ColorQuest XE instrument operated in transmission mode. The solutions were then heated to 95° C., held at this temperature for 30 seconds and then immediately cooled to room temperature in an ice bath. The clarity of the heat treated solutions was then measured again.

The clarity of the protein solutions before and after heating is set forth in the following Table 37.

TABLE 37

Effect of heat treatment on clarity of 2% w/v protein solutions

| Product | pH | Haze before heat treatment (%) | Haze after heat treatment (%) |
|---|---|---|---|
| YP01-D11-11A YP701 | 3.89 | 2.6 | 0.9 |
| YP01-E19-11A YP701 | 3.99 | 7.6 | 7.1 |
| YP03-J05-11A YP701 | 3.73 | 5.4 | 3.0 |
| YP05-A18-12A YP701 | 3.38 | 0.0 | 0.0 |
| YP06-B06-12A YP701-01 | 3.59 | 0.0 | 0.0 |
| YP06-B07-12A YP701 | 3.56 | 0.0 | 0.0 |
| Propulse | 6.24 | 96.1 | 96.4 |
| Propulse (pH adjusted) | 3.00 | 96.6 | 96.6 |
| Nutralys S85F | 7.44 | 97.2 | 97.1 |
| Nutralys S85F (pH adjusted) | 3.00 | 97.2 | 97.1 |
| Pisane C9 | 7.76 | 97.6 | 97.5 |
| Pisane C9 (pH adjusted) | 3.00 | 97.4 | 97.6 |

As may be seen from the results presented in Table 37, the yellow pea protein isolates prepared as described in Example 24 produced solutions which were very low in haze before and after heat treatment. The solutions of commercial yellow pea protein product were highly cloudy before and after heating at natural pH and pH 3.

Example 31

This Example contains the solution color values determined for the yellow pea protein isolates prepared as described in Example 24 as well as the commercial yellow pea protein products.

Protein solutions were prepared by dissolving sufficient protein product to supply 0.48 g of protein in 15 ml of RO water. The pH of the solutions was measured with a pH meter and the color and clarity assessed using a HunterLab ColorQuest XE instrument operated in transmission mode. Hydrochloric acid solution was added to the samples of commercial yellow pea protein product to lower the pH to 3 and then the measurement repeated. The results obtained are set forth in the following Table 37.

TABLE 38

Color values for solutions of pulse product

| Product | pH | L* | a* | b* | Haze (%) |
|---|---|---|---|---|---|
| YP01-D11-11A YP701 | 3.45 | 93.97 | 0.54 | 12.70 | 5.0 |
| YP01-E19-11A YP701 | 3.79 | 95.44 | 0.09 | 8.62 | 14.2 |
| YP03-J05-11A YP701 | 3.62 | 93.64 | 0.52 | 10.97 | 6.0 |
| YP05-A18-12A YP701 | 3.44 | 96.51 | −0.35 | 9.29 | 0.0 |
| YP06-B06-12A YP701-01 | 3.57 | 96.77 | −0.39 | 8.74 | 1.5 |
| YP06-B07-12A YP701 | 3.43 | 96.42 | −0.35 | 9.32 | 2.1 |
| Propulse | 6.15 | 35.33 | 12.61 | 48.79 | 96.6 |
| Propulse (pH adjusted) | 3.00 | 37.83 | 11.55 | 47.87 | 96.9 |
| Nutralys S85F | 7.32 | 53.48 | 6.20 | 34.01 | 97.5 |
| Nutralys S85F (pH adjusted) | 3.00 | 53.70 | 7.00 | 32.66 | 97.4 |
| Pisane C9 | 7.68 | 45.04 | 8.57 | 47.57 | 98.8 |
| Pisane C9 (pH adjusted) | 3.00 | 46.62 | 8.30 | 45.88 | 98.3 |

As may be seen from the results presented in Table 38, the yellow pea protein isolates prepared as described in Example 24 produced solutions that were low in haze and lighter, less red and less yellow than the solutions of commercial pea protein product.

SUMMARY OF THE DISCLOSURE

In summary of this disclosure, the present invention provides novel pulse protein products which are completely soluble and form heat stable, preferably transparent, solutions at acid pH and are useful in the protein fortification of aqueous systems, including soft drinks and sport drinks, without leading to protein precipitation. Modifications are possible within the scope of this invention.

What we claim is:

1. A pulse protein product having a protein content of at least about 60 wt % (N×6.25) d.b. and which
   is completely soluble at 1% w/v in water at acid pH values of less than about 4.4,
   is heat stable in aqueous media at acid pH values in the range of about 1.5 to about 4.4, such heat stability being determined by heating a 2% w/v aqueous protein solution of the pulse protein product at 95° C. for 30 seconds followed by cooling the heated solution to room temperature in an ice bath and measuring the clarity of the cooled solution in comparison to the clarity of the aqueous solution prior to heating,
   does not require stabilizers or other additives to maintain the protein product in solution,
   is low in phytic acid
   requires no enzymes in the production thereof.

2. The pulse protein product of claim 1 that has a clean flavor and no off odors.

3. The pulse protein product of claim 1 wherein the pulse protein has not been hydrolyzed.

4. The pulse protein product of claim 1 which is low in trypsin inhibitor activity.

5. The pulse protein product of claim 1 which has a protein content of at least about 90 wt % (N×6.25) d.b.

6. The protein product of claim 1 which has a protein content of about 100 wt % (N×6.25) d.b.

7. The pulse protein product of claim 1 which has a phytic acid content of less than about 1.5 wt %.

8. A pulse protein product having:
   1. a molecular weight profile which is:
      75 to 85%>100,000 Da
      10 to 18%>15,000-100,000 Da
      2 to 5%>5,000-15,000 Da
      1 to 4%>1000-5000 Da,
   2. a protein content of at least about 60 wt % (N×6.25) d.b.; and
   3. a solubility at 1% protein w/v in water at a pH of about 2 to about 4 of greater than about 90%.

9. The pulse protein product of claim 8 which is a yellow pea protein product.

10. A pulse protein product which is a lentil or dry pea protein product and which has a protein content of at least about 60 wt % (N×6.25) d.b., which has a solubility at 1% protein w/v in water at a pH of about 2 to about 4 of greater than about 90%, and which has an absorbance of visible light at 600 nm (A600) for a 1% protein w/v aqueous solution at a pH of over the range of 2 to 4 of less than 0.150.

11. The pulse protein product of claim 10 which is a yellow pea protein product.

12. A pulse protein product which is a lentil or dry pea protein product and having a protein content of at least about 60 wt % (N×6.25) d.b. which has an absorbance of visible light at 600 nm (A600) for an unheated 1% w/v protein aqueous solution at a pH in the range of 2 to 4 of less than 0.150.

13. The pulse protein product of claim 12 which is a yellow pea protein product.

14. A pulse protein product having a protein content of at least about 60 wt % (N×6.25) d.b. which has a haze reading for an unheated 1% w/v protein aqueous solution at a pH over the range of 2 to 4, of less than 15%.

15. The pulse protein product of claim 14 which is a yellow pea protein product.

16. A pulse protein product having a protein content of at least about 60 wt % (N×6.25) d.b. which has a haze reading for a 2% protein w/v solution in water at a pH over the range of 2 to 4, after heat treatment at 95° C. for 30 seconds, of less than 15%.

17. The pulse protein product of claim 16 which is a yellow pea protein product.

18. The pulse protein product of any one of claim 10 or 12 or 14 or 16 which has a protein content of at least about 90 wt % (N×6.25) d.b.

19. A pulse protein product having a protein content of at least about 60 wt % (N×6.25) d.b. which has colorimeter readings of L*=about 92 to about 100, a*=about −1 to about 1 and b*=0 to about 14, for a solution thereof in water prepared by dissolving sufficient pulse protein product to supply 3.2 g of protein per 100 ml of water, and having a pH of less than about 4.4 without the subsequent addition of a pH adjusting agent.

20. The pulse protein product of claim 19 which is a yellow pea protein product.

21. The pulse protein product of claim 19 which has a protein content of at least about 90 wt % (N×6.25) d.b.

22. The pulse protein product of claim 7 which has a phytic acid content of less than about 0.5 wt %.

23. The pulse protein product of claim 12 wherein the A600 value is less than about 0.100.

24. The pulse protein product of claim 23 wherein the A600 value is less than 0.050.

25. The pulse protein product of claim 14 wherein the haze reading is less than about 10%.

26. The pulse protein product of claim 25 wherein the haze reading is less than about 5%.

27. The pulse protein product of claim 16 wherein the haze reading is less than about 10%.

28. The pulse protein product of claim 27 wherein the haze reading is less than about 5%.

29. The pulse protein product claimed in claim 21 wherein the protein content is about 100 wt % (N×6.25).

\* \* \* \* \*